United States Patent
Kim et al.

(10) Patent No.: US 10,751,350 B2
(45) Date of Patent: Aug. 25, 2020

(54) METHOD FOR OBTAINING VITAMIN D2 FROM SHIITAKE MUSHROOMS

(71) Applicant: JANGHEUNG COUNTY RESEARCH INSTITUTE FOR MUSHROOM INDUSTRY, Jeollanam-do (KR)

(72) Inventors: Kyung-Je Kim, Jeollanam-do (KR); Kyoung Sun Seo, Jeollanam-do (KR); Tae-Young Park, Jeollanam-do (KR); Seong-Woo Jin, Jeollanam-do (KR); Bong-Suk Choi, Jeollanam-do (KR); Jin-Kyeong Kim, Jeollanam-do (KR)

(73) Assignee: JANGHEUNG COUNTY RESEARCH INSTITUTE FOR MUSHROOM INDUSTRY, Jeollanam-Do (KR)

( * ) Notice: Subject to any disclaimer, the term of this patent is extended or adjusted under 35 U.S.C. 154(b) by 311 days.

(21) Appl. No.: 15/517,074

(22) PCT Filed: Oct. 20, 2015

(86) PCT No.: PCT/KR2015/011059
§ 371 (c)(1),
(2) Date: Apr. 5, 2017

(87) PCT Pub. No.: WO2016/064161
PCT Pub. Date: Apr. 28, 2016

(65) Prior Publication Data
US 2017/0304324 A1     Oct. 26, 2017

(30) Foreign Application Priority Data

Oct. 22, 2014  (KR) .................. 10-2014-0143208

(51) Int. Cl.
*A61K 31/592* (2006.01)
*A61K 36/07* (2006.01)

(52) U.S. Cl.
CPC ............ *A61K 31/592* (2013.01); *A61K 36/07* (2013.01); *A61K 2236/33* (2013.01); *A61K 2236/37* (2013.01)

(58) Field of Classification Search
CPC .................................................. A61K 36/07
See application file for complete search history.

(56) References Cited

U.S. PATENT DOCUMENTS

2014/0088049 A1*  3/2014  Chalupa ............... A23L 5/32
                                             514/167

FOREIGN PATENT DOCUMENTS

| KR | 10-0385335 B1    | 5/2003 |
|----|------------------|--------|
| KR | 10-2008-0057774 A | 6/2008 |
| KR | 10-2011-0043224 A | 4/2011 |
| KR | 10-2011-0090180 A | 8/2011 |
| KR | 10-1168747 B1    | 7/2012 |
| KR | 10-2014-0094845 A | 7/2014 |

OTHER PUBLICATIONS

Stamets, P. Place Mushrooms in Sunlight to Get your Vitamin D. Internet Publication Date: Aug. 16, 2012. [Retrieved from the internet on: May 13, 2019]. Retrieved from: <URL: https://fungi.com/blogs/articles/place-mushrooms-in-sunlight-to-get-your-vitamin-d>. (Year: 2012).*
Newell et al. Applied and Environmental Microbiology, Jul. 1988. p. 1876-1879. (Year: 1988).*
Keegan et al. Dermato-Endocrinology 5:1, Jan./Feb./Mar. 2013. pp. 165-176. (Year: 2013).*
Wei-Jie Wu et al., "Statistical Optimization of Ultraviolet Irradiate Conditions for Vitamin D2 Synthesis in Oyster Mushrooms (Pleurotus ostreatus) Using Response Surface Methodology", PLoS One. Apr. 15, 2014;9(4):e95359. doi:10.1371/journal.pone.0095359. eCollection 2014.
Abstract of Ko et al., Effect of UV-B Exposure on the Concentration of Vitamin D2 in Sliced Shiitake Mushroom (Lentinus edodes) and White Button Mushroom (Agaricus bisporus), J. Agric. Food Chem. 2008, 56, 10, 3671-3674.

* cited by examiner

*Primary Examiner* — Amy L Clark
(74) *Attorney, Agent, or Firm* — The PL Law Group, PLLC

(57) ABSTRACT

A method of obtaining vitamin D from shiitake includes a) adding ethanol to shiitake powder, followed by reflux extraction, to prepare a shiitake extract; and (b) irradiating ultraviolet (UV) light to the shiitake extract prepared in step (a). When shiitake extracts are obtained and exposed to ultraviolet light under specific conditions, the content of vitamin D2 in the shiitake extracts may be increased.

5 Claims, 2 Drawing Sheets

METHOD FOR OBTAINING VITAMIN D2 FROM SHIITAKE MUSHROOMS

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2015/011059, filed Oct. 20, 2015, which claims priority to the benefit of Korean Patent Application No. 10-2014-0143208 filed in the Korean Intellectual Property Office on Oct. 22, 2014, the entire contents of which are incorporated herein by reference.

TECHNICAL FIELD

The present disclosure relates to a method for obtaining vitamin D2 from shiitake, the method including (a) adding ethanol to shiitake powder, followed by reflux extraction, to prepare a shiitake extract; and (b) irradiating ultraviolet (UV) light to the shiitake extract prepared in step (a).

BACKGROUND ART

Shiitake is a mushroom belonging to *Lentius* genus of Agaricales Pleurotaceae family of Basidiomycetes. Shiitake is a wood-borne fungus that parasitizes in broad-leaved trees such as oak and beech trees in the temperate region from spring to autumn, and Shiitake grows alone or in clusters in a tree stump or a stump of a broad-leaved tree. Together with oyster mushrooms, Shiitake has been widely used for edible purposes for a long time, and is one of mushrooms that are grown actively in a commercial way due to artificial cultivation.

Shiitake is rich in various minerals and vitamins, and also contains fiber that helps digestion in stomach and small intestine. Thus, shiitake is good for obesity, diabetes, heart disease, and liver disease. Shiitake is also rich in protein, calcium, phosphorus, iron, vitamin D which helps bones be in a good shape, vitamin B that is essential for hematopoiesis, and ellatethene which helps blood metabolism. Sun-dried shiitake is about twice as nutritious as fresh shiitake. In particular, sun-dried shiitake is rich in vitamin D, which helps the absorption of calcium. In this aspect, shiitake strengthens teeth and prevents osteoporosis.

Vitamin D is an important nutrient that facilitates absorption of calcium and phosphate in the intestine, transfers calcium from the calcified skeleton to the blood, and helps calcium and phosphate to be re-absorbed by the kidney. Up to now, D2 to D7 have been found as vitamin D, and from among these, D2 and D3 are biologically active. Due to ultraviolet (UV) light irradiation, vitamin D2 (ergocalciferol) is synthesized from ergosterol that is plant sterol and vitamin D3 (cholecalciferol) is synthesized from cholesterol that is an animal sterol. Vitamin D synthesized as described above is converted into the active form of 1,25-dihydroxyvitamin D in the kidney via the liver, and 1,25-dihydroxyvitamin D promotes the synthesis of calcium-binding-proteins in the small intestine, thereby helping calcium to be absorbed. When the concentration of the active vitamin D is increased, the intestine absorbs more calcium, leading to a higher calcium concentration in the blood.

Since vitamin D is biosynthesized in the body when exposed to the sun, unlike other nutrients that need to be supplied only as food, vitamin D is considered as a less important nutrient. Recently, the use of various sunscreen products to block UV light limits the time for exposure to UV light, thereby hindering the biosynthesis of vitamin D in the skin. In particular, in the case of the menopausal women and the elderly, less exposure to UV light may mean an extreme limitation on the biosynthesis of vitamin D. Accordingly, the supply of vitamin D via the diet is inevitable. Vitamin D that can be ingested via diet is present in large amounts in mushrooms and fish, and in small amounts in egg yolks, milk and dairy products. However, not only limited number of foods provides vitamin D via diet, but the amount of vitamin D contained in such foods is very low. Accordingly, the supply of vitamin D via foods is very limited. In the United States, vitamin D-fortified foods, such as milk, dairy products, orange juice, and nutrition bars, are being sold to compensate for the lack of vitamin D. In Korea, vitamin D-fortified milk is commercially available, but there are only few vitamin D-fortified products. Therefore, there is a need to develop vitamin D-enriched foods.

Korean Patent No. 1168747 discloses a method of cultivating oyster mushrooms of which the ergosterol content is enhanced by LED illumination. However, the disclosed method is different from the method of obtaining vitamin D2 from shiitake mushrooms according to the present disclosure.

SUMMARY

The present disclosure provides a method of obtaining vitamin D from shiitake effectively by optimizing a portion of shiitake, an extraction solvent, an extraction method, and ultraviolet (UV) light exposure conditions, and a processed food containing vitamin D2 obtained by the above method.

According to one or more embodiments, a method of obtaining vitamin D from shiitake includes (a) adding ethanol to shiitake powder, followed by reflux extraction, to prepare a shiitake extract; and (b) irradiating ultraviolet (UV) light to the shiitake extract prepared in step (a).

According to one or more embodiments, provided is a processed food containing vitamin D2 that is obtained by using the method.

When shiitake extracts are obtained and exposed to ultraviolet light under specific conditions according to the present disclosure, the content of vitamin D2 in the shiitake extracts is substantially increased. Accordingly, the method of obtaining vitamin D2 from shiitake according to the present disclosure may optimize the use of the active ingredient of shiitake, and may also be useful for use in processed foods for the compensation for vitamin D2 and medical products for the prevention and treatment of disease associated with the lack of vitamin D2.

DETAILED DESCRIPTION

Figure 1:
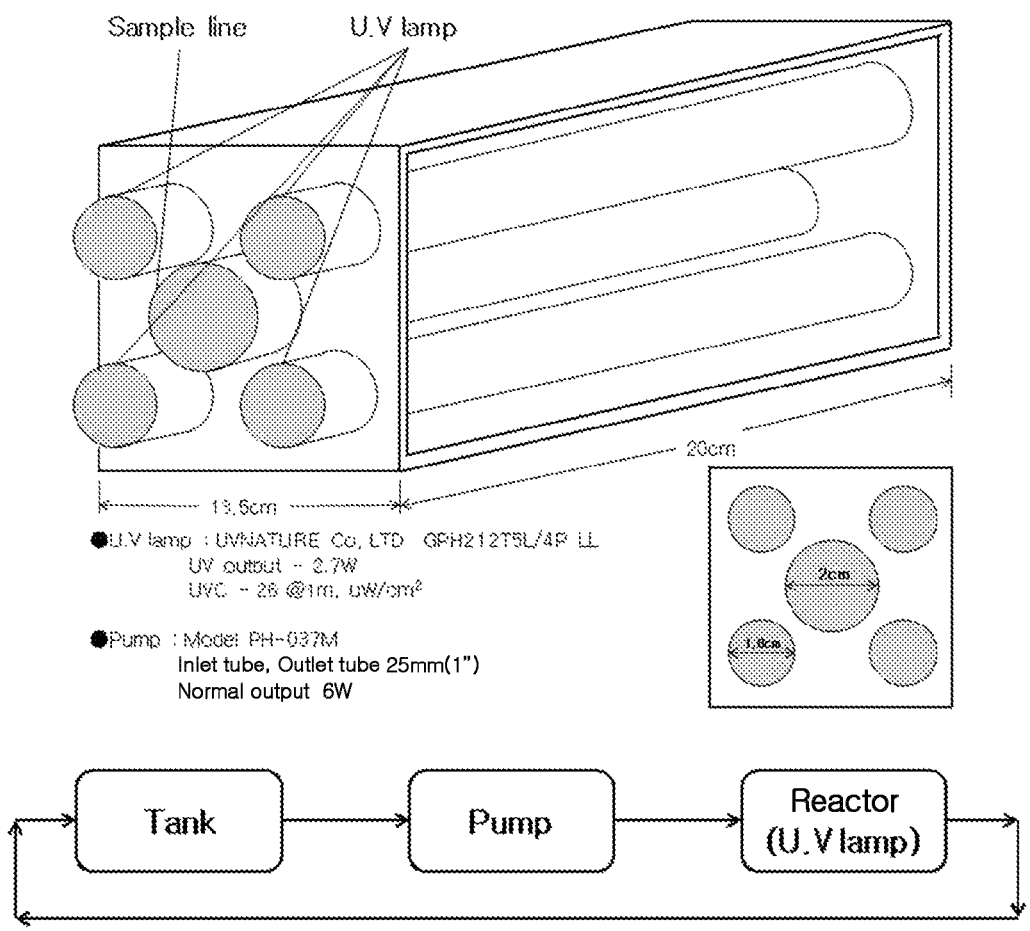
FIG. 1 shows the picture of an ultraviolet (UV) light irradiation device and a schematic view of the UV radiation device.

The present disclosure provides a method of obtaining vitamin D from shiitake, the method including:

a) adding ethanol to shiitake powder, followed by reflux extraction, to prepare a shiitake extract; and (b) irradiating ultraviolet (UV) light to the shiitake extract prepared in step (a).

In the method of obtaining vitamin D2 according to the present disclosure, the shiitake in step (a) may be the pileus of shiitake. The pileus of shiitake has more ergosterol than the stipe of shiitake, and thus, after exposure to UV light, may produce more vitamin D2.

In the method of obtaining vitamin D2 according to the present disclosure, in one embodiment, the reflux extraction in step (a) may be performed at a temperature of 75° C. to 85° C. for 1 hour to 3 hours after adding 90% (v/v) to 100% (v/v) of ethanol to shiitake powder; and in one embodiment, the reflux extraction in step (a) may be performed at a temperature of 80° C. for 2 hours after 100% (v/v) of ethanol was added to shiitake powder. When shiitake extracts are obtained by using the extraction solvents and the extraction methods described above, the ergosterol content in shiitake extracts may be increased compared to when other extraction solvents and other extraction methods are used.

In the method of obtaining vitamin D2 according to the present disclosure, in one embodiment, the UV light may be irradiated to 80 mL of 120 mL of the shiitake extract by using three to five UV lamps, each transmitting UV light having the intensity of 24 µW/cm² to 28 µW/cm², at a time for 3 minutes, or one of such lamps for 16 minutes to 20 minutes; and, in one embodiment, the UV light may be irradiated to 100 mL of the shiitake extract by using four UV lamps, each transmitting UV light having the intensity of 26 µW/cm², for 3 minutes, or one of such UV lamps for 18 minutes. In one embodiment, the UV lamps may each have a wavelength of 250 nm to 260 nm. In one embodiment, the UV lamps may each have a wavelength of 254 nm. The UV light irradiation under these conditions may effectively convert ergosterol, which is the precursor of vitamin D2 in the shiitake extract, into vitamin D2.

In one embodiment, the method of obtaining vitamin D2 from shiitake includes (a) adding 90 to 100% (v/v) of ethanol to powder of the pileus of shiitake, followed by reflux extraction at a temperature of 75° C. to 85° C. for 1 hour to 3 hours to prepare a shiitake extract; and (b) irradiating UV light to 80 mL to 120 mL of the shiitake extract prepared in step (a) by using three to five UV lamps for 3 minutes or one UV lamp for 16 minutes to 20 minutes, each UV lamp transmitting UV light having the intensity of 24 µW/cm² to 28 µW/cm².

In one embodiment, the method of obtaining vitamin D2 from shiitake includes (a) adding 100% (v/v) of ethanol to powder of the pileus of shiitake, followed by reflux extraction at a temperature of 80° C. for 2 hours to prepare a shiitake extract; and (b) irradiating UV light to 100 mL of the shiitake extract prepared in step (a) by using four UV lamps for 3 minutes or one UV lamp for 18 minute, each UV lamp transmitting UV light having the intensity of 26 µW/cm².

An embodiment of the present disclosure provides a processed food containing vitamin D2 that is obtained by using one of the methods. The kind of the processed food is not particularly limited. Examples of foods, to which vitamin D2 can be added, include meat, sausage, bread, chocolate, candy, snack, confectionery, pizza, instant noodles and other noodles, gums, dairy products including ice cream, various soups, drinks, tea, alcoholic beverages, and vitamin complexes, and includes processed foods in a conventional sense.

Hereinafter, embodiments of the present disclosure will be described in detail. However, the embodiments are provided for illustrative purpose only, and do not limit the scope of the present disclosure.

Experimental Methods

1. Searching for Method of Extracting Ergosterol from Shiitake

Dried shiitake was milled to a size of 100 mesh, and an extract thereof was obtained therefrom by using 100% ethanol. Other extraction methods were used to search for an optimal ethanol extraction method. Extraction methods used herein were a reflux extraction, an ultrasonic extraction, a shaking extraction, and a stirring extraction. The reflux extraction was performed at 80° C. for 2 hours, the ultrasonic extraction was performed for 20 minutes, and the shaking extraction and the stirring extraction were each performed at room temperature for 2 hours. The obtained extracts were pretreated according to an ergosterol measurement method, and then, subjected to HPLC.

2. Searching for Solvent for Extracting Ergosterol from Shiitake

Dried shiitake was milled to a size of 100 mesh, and then, various extraction solvents were used to search for an optimal ergosterol extraction solvent. Extraction solvents used herein were 100% ethanol, 80% ethanol, 60% ethanol, 40% ethanol, 20% ethanol, and distilled water, and extracts obtained by the reflux extraction using these extraction solvents were pretreated according to an ergosterol measurement method and then, subjected to HPLC.

3. Comparing Amounts of Ergosterol and Vitamin D2 Depending on Portion of Shiitake The amounts of vitamin D2 and ergosterol according to a portion of shiitake were analyzed. In detail, a shiitake mushroom was dried, and then, divided into the stipe and the pileus and milled to a size of 100 mesh, thereby preparing samples. The samples were subjected to reflux extraction at a temperature of 80° C. for 2 hours by using 100% ethanol, and then, the samples were divided into samples that had not been exposed to UV light and samples that had been exposed to UV light for 3 minutes, and pretreated according to a method of measuring ergosterol and vitamin D2, and subjected to HPLC.

4. Searching for Optimal UV Light Irradiation Conditions for the Conversion of Ergosterol into Vitamin D2

Optimal UV light irradiation conditions for the conversion of ergosterol, which is the precursor of vitamin D2 in shiitake, into vitamin D2 were searched for. In detail, UV light was irradiated by using different numbers of UV lamps for different exposure times to measure the amounts of vitamin D2 and ergosterol.

To determine an appropriate irradiation time when four UV lamps (GPH212T5L, UVNATURE Co. LTD), each having a wavelength of 254 nm and the UV intensity of 26 µW per cm² area and located away from samples in a distance of 1 m, were used, 100 mL of shiitake extracts obtained by reflux extraction using 100% ethanol were simultaneously exposed to the four UV lamps, and the irradiation time was set from 1 minute to 120 minutes. To determine an appropriate irradiation time when one UV lamp was used, samples obtained by reflux extraction were exposed to one UV lamp, and the irradiation time was set from 3 minutes to 33 minutes. Extracts that had been exposed to UV light were pretreated according to a method of measuring ergosterol and vitamin D2, and subjected to HPLC.

5. Measuring Amounts of Ergosterol and Vitamin D2

Amounts of ergosterol and vitamin D2 were measured. In detail, 100 mL of ethanol was added to 5 g of a sample, and then, reflux extraction was performed on the result for 1 hour. The supernatant was collected, and 100 mL of ethanol was added to the residual, and reflux extraction was performed thereon at a temperature of 80° C. for 1 hour. 20 mL of ethanol and 10 g of potassium hydroxide were added to an ethanol extract, and the mixture was saponified at 80° C. for 1 hour. To the saponified solution, 50 mL of distilled water was added, and the resultant mixture was divided into two 50 mL portions by using hexane. A hexane layer was then completely concentrated, and the concentrated hexane layer was dissolved in 5 mL of methanol and subjected to HPLC.

TABLE 1

HPLC analysis conditions

| Item | Analysis conditions |
|---|---|
| Instrument | Agilent Technologies 1200 Series |
| Column | Agilent XDB-$C_{18}$ (Method Development Kit) (4.6 × 150 mm, 5 um) |
| Solvent | 98% Methanol |
| Column temp. | 28.8° C. |
| Wavelength | UV 280 nm |
| Flow rate | 1.0 mL/min |
| Injection volume | 20 μL |

6. Cytotoxicity of Shiitake Extracts

Cytotoxicity tests were performed on extracts obtained by reflux extraction at a temperature of 80° C. for 2 hours. Cytotoxicity of the extracts was measured by using 3-(4,5-dimethyl-2-thiazolyl)-2,5-diphenyl-2H-tetrazolium bromide (MTT). Cultured Vero cells were spread on a 96-well plate at the cell population of $1 \times 10^5$ cells/well and attached and stabilized thereon by 24 hours of incubation. Then, the cells were treated with samples diluted at a concentration of 10, 50, 100 and 500 μg/mL and cultured for 24 hours. Medium used was replaced with a fresh medium, to which 0.5 μg/mL tetrazolium-based colorimetric (MTT) was added to form formazan for four hours. When a reaction was completed, the medium was removed, formazan was dissolved in 150 μl of DMSO, and the absorption of the result was measured at a wavelength of 540 nm. Cell viability of each sample was measured relatively with reference to 100% of an untreated group.

Example 1: Ergosterol Content According to Shiitake Extraction Method

To search for an optimal method of extracting ergosterol, which is a precursor of vitamin D in shiitake, reflux extraction, ultrasonic extraction, shaking extraction, and stirring extraction were performed. The obtained results are shown in Table 2. Reflux extraction was performed at a temperature of 80° C. for 2 hours, and showed the greatest ergosterol content of 153.95 mg % from among the used extraction methods. The ergosterol content for the ultrasonic extraction was 51.01 mg %, the ergosterol content for the shaking extraction was 21.78 mg %, and the stirring extraction showed the smallest extraction content of 16.41 mg %.

TABLE 2

Ergosterol content (mg %) according to shiitake extraction method

| | Extraction method | | | |
|---|---|---|---|---|
| | Reflux extraction | Ultrasonic extraction | Shaking extraction | Stirring extraction |
| Ergosterol (mg %) | 153.95 ± 7.15 | 51.01 ± 1.41 | 21.78 ± 6.61 | 16.41 ± 0.57 |

Example 2: Ergosterol Content According to Shiitake Extraction Solvent

To search for an optimal solvent for extracting ergosterol of shiitake, 100% ethanol, 80% ethanol, 60% ethanol, 40% ethanol, 20% ethanol, and distilled water were used for reflux extraction, and results obtained therefrom are shown in Table 3. When 100% ethanol was used for extracting shiitake, the obtained ergosterol was the greatest, that is, 105.91 mg %, and when 20% ethanol was used, the ergosterol content was the lowest, that is, 0.48 mg %. When water was used for extraction, ergosterol was not extracted, and the lower the ethanol concentration, the lower the ergosterol content.

TABLE 3

Ergosterol content (mg %) according to shiitake extraction solvent

| | Extraction solvent | | | | | |
|---|---|---|---|---|---|---|
| | Ethanol | | | | | |
| | 100% | 80% | 60% | 40% | 20% | Water |
| Ergosterol (mg %) | 105.91 ± 3.27 | 44.09 ± 0.19 | 36.17 ± 0.09 | 18.16 ± 0.60 | 0.48 ± 0.03 | — |

Example 3: Vitamin D2 Content and Ergosterol Content According to Portion of Shiitake Shiitake was divided into the stipe and the pileus, and then, extraction was performed thereon to measure amounts of vitamin D2 and ergosterol. Results obtained therefrom are shown in Table 4. In the case of extracts that had not been exposed to UV light, vitamin D2 was not measured. The ergosterol content in the stipe was 383.00 mg %, and the ergosterol content in the pileus was 471.48 mg %. In the case of extracts that had been exposed to UV light, the vitamin D2 content in the stipe was 78.41 mg %, and the vitamin D2 content in the pileus was 91.26 mg %.

TABLE 4

Vitamin D2 content and Ergosterol content according to portion of shiitake (mg %)

| UV light irradiation time | Shiitake stipe | | Shiitake pileus | |
|---|---|---|---|---|
| min | Vitamin D2 | Ergosterol | Vitamin D2 | Ergosterol |
| 0 minutes | 0 | 383.00 ± 0.67 | 0 | 471.48 ± 5.33 |
| 3 minutes | 78.41 ± 0.37 | 104.68 ± 0.17 | 91.26 ± 9.64 | 71.46 ± 2.46 |

Example 4: Vitamin D2 Content and Ergosterol Content According to UV Light Irradiation Conditions To search for optimal UV light irradiation conditions to convert ergosterol, which is the precursor of vitamin D2 in shiitake, into vitamin D2, UV light was irradiated according to the number of UV lamps and time to measure vitamin D2 and ergosterol. Results obtained therefrom are shown in Tables 5 and 6. When four UV lamps were used, an extract that had been exposed to UV light for 3 minutes had the greatest vitamin D2 content, that is, 104.89 mg %. The longer UV light irradiation time, the vitamin D2 content was gradually decreased, and at 90 minutes or more of UV irradiation, the vitamin D2 content was as low as 5 mg %. In the case of ergosterol, an extract that had not been exposed to UV light had the greatest ergosterol content, that is, 471.48 mg %. The longer UV light irradiation time, the lower ergosterol content. At 10 minutes or more of UV light irradiation, the ergosterol content was as low as 4 mg % to 8 mg % (Table 5).

When one UV lamp was used, the vitamin D2 content had the greatest value of 116.55 at 18 minutes, and when UV light was not irradiated, vitamin D2 was not produced, and when the UV irradiation time reached 3 minutes, the vitamin D2 content was 63.68 mg % and, up to 18 minutes, was gradually increased, and at greater than 18 minutes, the vitamin D2 content was decreased. Regarding to the ergosterol content, an extract that had not been exposed to UV light and an extract that had been exposed to UV light for 3 minutes had the ergosterol contents of 471.48 mg % and 437.99 mg %, respectively. The longer UV light irradiation time, the smaller ergosterol content (Table 6). It was confirmed that, in converting ergosterol, which is the precursor of vitamin D2 in shiitake, into vitamin D2, the greater number of UV lamps, the shorter time.

TABLE 5

Vitamin D2 content and ergosterol content (mg %) according to irradiation time when four UV lamps were used

| UV light irradiation time (min) | Vitamin D2 (mg %) | Ergosterol (mg %) |
|---|---|---|
| Control | 0 | 471.48 ± 3.90 |
| 1 | 82.39 ± 0.57 | 133.26 ± 1.50 |
| 2 | 97.00 ± 0.69 | 126.86 ± 1.32 |
| 3 | 104.89 ± 0.60 | 55.77 ± 0.54 |
| 4 | 91.26 ± 0.18 | 71.46 ± 0.69 |
| 5 | 94.30 ± 0.21 | 30.64 ± 0.45 |
| 10 | 81.41 ± 0.97 | 5.87 ± 0.18 |
| 30 | 14.77 ± 0.54 | 8.25 ± 2.18 |
| 60 | 10.12 ± 0.08 | 4.36 ± 0.86 |
| 90 | 5.43 ± 0.30 | 6.69 ± 1.80 |
| 120 | 5.51 ± 0.38 | 5.27 ± 0.50 |

TABLE 6

Vitamin D2 content and ergosterol content (mg %) according to irradiation time when one UV lamp was used

| UV light irradiation time (min) | Vitamin D2 (mg %) | Ergosterol (mg %) |
|---|---|---|
| Control | 0 | 471.48 ± 3.90 |
| 3 | 63.68 ± 0.23 | 437.99 ± 0.47 |
| 6 | 93.79 ± 0.30 | 370.39 ± 0.69 |
| 9 | 107.30 ± 0.31 | 272.96 ± 0.51 |
| 12 | 107.23 ± 0.39 | 215.01 ± 0.33 |
| 15 | 101.38 ± 0.64 | 241.01 ± 0.46 |
| 18 | 116.55 ± 0.63 | 220.42 ± 0.57 |
| 33 | 99.12 ± 0.01 | 148.67 ± 0.33 |

Figure 2:
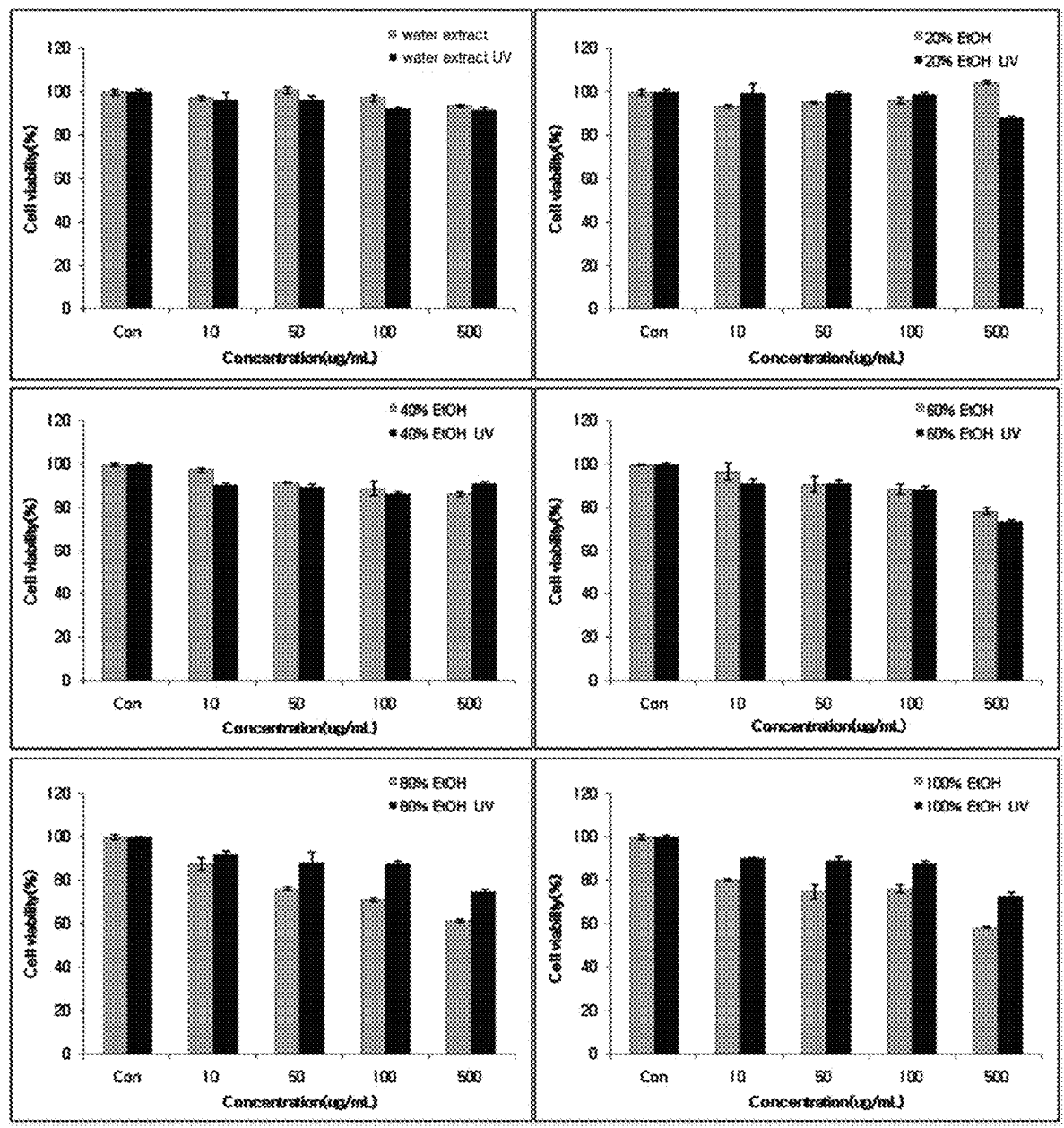
FIG. 2 shows a graph of cell viability of shiitake extracts depending on UV light irradiation.

Example 5: Cytotoxicity of Shiitake Extracts According to UV Light Irradiation Cytotoxicity stability of shiitake extracts was evaluated according to UV light irradiation. Results obtained therefrom are shown in FIG. 2. In the case of shiitake extracts obtained using 80% ethanol and 100% ethanol, an extract that had been exposed to UV light showed lower cytotoxicity than an extract that had not been exposed to UV light.

What is claimed is:

1. A method of obtaining vitamin D from shiitake, the method comprising:
    adding ethanol to shiitake powder, followed by reflux extraction, to prepare a shiitake extract; and
    irradiating the prepared shiitake extract with ultraviolet (UV) light with either three to five UV lamps for 3 minutes or one UV lamp for 16 minutes to 20 minutes, each UV lamp transmitting UV light with an intensity in a range of 24 $\mu W/cm^2$ to 28 $\mu W/cm^2$.

2. The method of claim 1, wherein the reflux extraction is performed at a temperature of 75° C. to 85° C. for 1 to 3 hours after the ethanol is added to the shiitake powder.

3. The method of claim 1,
    wherein the shiitake powder to which the ethanol is added is powder of pileus of the shiitake; and
    the reflux extraction is performed at a temperature of 75° C. to 85° C. for 1 hour to 3 hours.

4. The method of claim 1, wherein the irradiating comprises using the three to five UV lamps for 3 minutes or the one UV lamp for 16 minutes to 18 minutes.

5. The method of claim 1, wherein the irradiating comprises using four UV lamps for 3 minutes or the one UV lamp for 18 minutes.

\* \* \* \* \*